United States Patent [19]

Eidenschink et al.

[11] Patent Number: 4,490,305

[45] Date of Patent: Dec. 25, 1984

[54] LIQUID-CRYSTALLINE HALOGEN COMPOUNDS, PROCESS FOR THEIR PREPARATION, DIELECTRICS CONTAINING THESE, AND ELECTRO-OPTICAL DISPLAY ELEMENT

[75] Inventors: Rudolf Eidenschink, Dieburg; Michael Römer, Rodgau; Georg Weber, Erzhausen, all of Fed. Rep. of Germany

[73] Assignee: Merck Patent Gesellschaft mit beschrankter Haftung, Darmstadt, Fed. Rep. of Germany

[21] Appl. No.: 418,360

[22] Filed: Sep. 15, 1982

[30] Foreign Application Priority Data

Sep. 15, 1981 [DE] Fed. Rep. of Germany ....... 3136624

[51] Int. Cl.³ .............. G02F 1/13; C09K 3/34; C07C 25/18; C07C 43/22; C07C 121/64
[52] U.S. Cl. .............. 260/465 F; 260/465 G; 252/299.5; 252/299.63; 252/299.66; 350/350 R; 350/350 S; 570/129; 570/182; 568/642; 568/643
[58] Field of Search ........... 252/299.5, 299.63, 299.66; 350/350 R, 350 S; 570/129, 182; 568/642, 643, 645, 647; 260/465 F, 465 G

[56] References Cited

U.S. PATENT DOCUMENTS

| | | |
|---|---|---|
| 3,947,375 | 3/1976 | Gray et al. .......... 252/299.66 |
| 4,130,502 | 12/1978 | Eidenschink et al. .......... 252/299.63 |
| 4,211,666 | 7/1980 | Imukai et al. .......... 252/295.6 |
| 4,216,109 | 8/1980 | Mizukuchi .......... 252/299.65 |
| 4,263,457 | 4/1981 | Takeda et al. .......... 570/129 |
| 4,302,352 | 11/1981 | Eidenschink et al. .......... 252/299.63 |
| 4,331,552 | 5/1982 | Eidenschink et al. .......... 252/299.63 |
| 4,340,498 | 7/1982 | Sugimori .......... 252/299.5 |
| 4,368,135 | 1/1983 | Osman .......... 252/295.5 |
| 4,405,488 | 9/1983 | Sugimori et al. .......... 252/299.5 |
| 4,415,470 | 11/1983 | Eidenschink et al. .......... 252/299.63 |

FOREIGN PATENT DOCUMENTS

| | | |
|---|---|---|
| 19665 | 12/1980 | European Pat. Off. ....... 252/299.63 |
| 47877 | 3/1982 | European Pat. Off. ....... 252/299.66 |
| 2636684 | 2/1978 | Fed. Rep. of Germany ... 252/299.5 |
| 2933563 | 2/1981 | Fed. Rep. of Germany ... 252/299.5 |
| 3205766 | 8/1983 | Fed. Rep. of Germany ......... 252/299.63 |
| 7343160 | 6/1974 | France ............... 570/129 |
| 5636568 | 4/1981 | Japan ............... 252/299.5 |
| 56150030 | 11/1981 | Japan ............... 252/299.5 |
| 5879938 | 5/1983 | Japan ............... 252/299.5 |
| 2039937 | 8/1980 | United Kingdom .......... 252/299.66 |

OTHER PUBLICATIONS

Marler; E. E. J. et al., J. Chem. Soc., pp. 266-271 (1937).
Tashiro; M. et al., J. Org. Chem., vol. 44, No. 17, pp. 3037-3041 (1979).
C. A., vol. 75, 102307w (1971).
Osman; M. A. et al., Mol Cryst. Liq. Cryst., vol. 82, (LETT), pp. 331-338 (1983).
C. A., vol. 93, 62827d (1980).
CAS, Registry Handbook, Number Section, 1980 Suppl., 74447-85-1, 74447-86-2.

Primary Examiner—Teddy S. Gron
Attorney, Agent, or Firm—Millen & White

[57] ABSTRACT

Liquid-crystalline halogen compounds of the formula

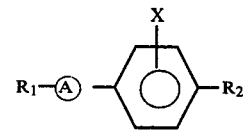

wherein the ring A is 1,4-phenylene or trans-1,4-cyclohexylene; $R_1$ is alkyl or alkoxy each of 1 to 12 carbon atoms or, when A is 1,4-phenylene, is also cyano; $R_2$ is alkyl or alkoxy each of 1 to 12 carbon atoms or, when A is 1,4-cyclohexylene, is also chlorine or bromine; and X is fluorine, chlorine or hydrogen; with the proviso that at least one of the substituents $R_2$ and X is a halogen atom are valuable components in liquid-crystalline dielectrics.

3 Claims, No Drawings

LIQUID-CRYSTALLINE HALOGEN COMPOUNDS, PROCESS FOR THEIR PREPARATION, DIELECTRICS CONTAINING THESE, AND ELECTRO-OPTICAL DISPLAY ELEMENT

BACKGROUND OF THE INVENTION

The properties of nematic or nematic-cholesteric liquid-crystalline materials of significantly varying their optical properties, such as light absorption, light scattering, birefringence, reflectivity or color, under the influence of electric fields, are widely utilized for electro-optical display elements. The functioning of display elements of this type is based, for example, on the phenomena of dynamic scattering, the deformation of aligned phases, the Schadt-Helfrich effect in the twisted cell or the cholesteric-nematic phase transition.

For the industrial application of these effects in electronic components, liquid-crystalline dielectrics are required which must meet a large number of demands. Chemical resistance to moisture, air and physical influences, such as heat, radiation in the infrared, visible and ultraviolet regions, and continuous and alternating electric fields, is of particular importance. Industrially usable liquid-crystalline dielectrics are also required to have a liquid-crystalline mesophase in the temperature range from at least 0° C. to +50° C., preferably from −10° C. to 60° C., and the lowest possible viscosity at room temperature, which preferably should not exceed $70 \times 10^{-3}$ Pa.s. Finally, they must not have any characteristic absorption in the region of visible light, that is to say they must be colorless.

A number of liquid-crystalline compounds have already been disclosed, which fulfill the stability demands made on dielectrics for electronic components, and which are also colorless. These include, in particular, the p,p'-disubstituted phenyl benzoates described in German Offenlegungsschrift No. 2,139,628 and the p,p'-disubstituted phenylcyclohexane derivatives described in German Offenlegungsschrift No. 2,636,684. In both classes of compounds, and also in other series of compounds with a liquid-crystalline mesophase, no individual compounds have hitherto been disclosed which form a liquid-crystalline nematic mesophase in the required temperature range from 0° C. to 60° C. As a rule, mixtures of two or more compounds are therefore prepared in order to obtain substances which can be used as liquid-crystalline dielectrics. For this purpose, at least one compound having a low melting point and clear point is usually mixed with another compound having a markedly higher melting point and clear point. This normally gives a mixture, the melting point of which is below that of the lower-melting component, while the clear point is between the clear points of the components. Nevertheless, difficulties arise again and again in the preparation of optimum dielectrics, because the components having the high melting points and clear points frequently also impart a high viscosity to the mixture. As a result, the switching times of the electro-optical display elements produced with these mixtures are extended in an undesirable manner.

Moreover, problems are frequently caused by the fact that the mutual solubility of the various components, in particular at room temperature or lower temperatures, is only very limited.

SUMMARY OF THE INVENTION

Accordingly, it is an object of this invention to prepare liquid-crystalline dielectrics which have a nematic phase within the required temperature range and, when used in liquid crystal cells, make switching times possible which are sufficiently short at room temperature.

Upon further study of the specification and appended claims, further objects and advantages of this invention will become apparent to those skilled in the art.

These objects have been attained by providing halogen compounds of Formula (I)

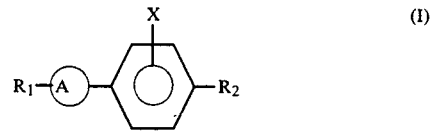

wherein the ring A is 1,4-phenylene or trans-1,4-cyclohexylene; $R_1$ is alkyl or alkoxy each of 1 to 12 carbon atoms or, when A is 1,4-phenylene, is also CN; $R_2$ is alkyl or alkoxy each of 1 to 12 carbon atoms or, when A is 1,4-cyclohexylene, is also chlorine or bromine; and X is fluorine, chlorine or hydrogen; with the proviso that at least one of the substituents $R_2$ and X is a halogen atom.

These compounds are outstandingly suitable as components of liquid-crystalline dielectrics. At the same time, these compounds have an extremely wide range of application.

Depending on the selection of the substituents, the compounds of Formula (I) can either be used as base materials representing the major component of liquid-crystalline dielectrics, or they can also be added in smaller proportions of, for example, 2 to 45 percent by weight to liquid-crystalline base materials from other classes of compounds, in order to prepare dielectrics having a widened liquid-crystalline mesophase or a lower viscosity, or to influence the magnitude of the dielectric anisotropy of such a dielectric.

By a suitable selection of the substituents $R_1$, $R_2$ and X, the compounds of Formula (I) can be used either for the preparation of dielectrics having a pronounced positive dielectric anisotropy, for use in display elements based on the twisted nematic cell or on the cholesteric-nematic phase transition, or it is also possible to prepare dielectrics having a dielectric anisotropy which only slightly differs from zero or is even negative. The latter dielectrics are useful in display elements based on dynamic scattering or on the deformation of aligned phases (DAP effect).

In the pure state, the compounds of Formula (I) are colorless, and they form liquid-crystalline mesophases in a temperature range which is astonishingly wide and is favorable for electro-optical applications.

The present invention thus relates to liquid-crystalline halogen compounds of Formula (I), to processes for their preparation and to their use as components of liquid-crystalline dielectrics. The invention also relates to liquid-crystalline dielectrics containing at least one liquid-crystalline halogen compound of Formula (I), and to electro-optical display elements based on a liquid crystal cell, which contain a liquid-crystalline dielectric of this type.

DETAILED DISCUSSION

The liquid-crystalline halogen compounds of Formula (I), according to this invention, comprise the chlorophenylcyclohexanes of Formula (Ia),

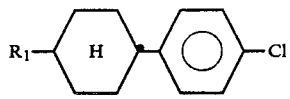

the fluorinated biphenyl derivatives of Formula (Ib),

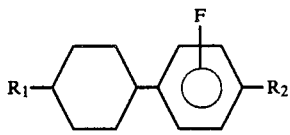

the bromophenylcyclohexanes of Formula (Ic),

the chlorinated biphenyl derivatives of Formula (Id),

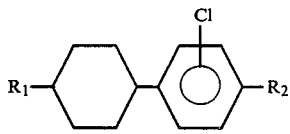

the fluorochlorophenylcyclohexanes of Formula (Ie),

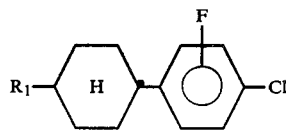

the fluorobromophenylcyclohexanes of Formula (If),

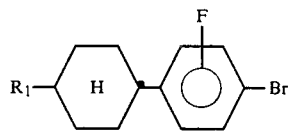

the dichlorophenylcyclohexanes of Formula (Ig),

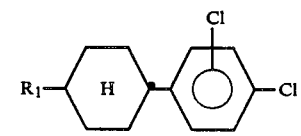

and the chlorobromophenylcyclohexanes of Formula (Ih),

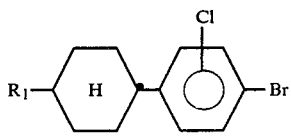

the substituents $R_1$ and $R_2$ being as defined for Formula (I).

If the liquid-crystalline halogen compounds of Formula (I) contain a 1,4-disubstituted cyclohexane ring, the substituents in the 1-position and 4-position are in a trans-arrangement relative to one another; in the graphic formulae, this is indicated by an enlarged black dot on the right-hand side of the ring.

The chloro- and bromo-phenylcyclohexanes of Formulae (Ia) and (Ic) have a positive dielectric anisotropy and a nematic mesophase situated in a more favorable temperature range than that of the analogous fluorophenylcyclohexanes according to U.S. Pat. No. 4,302,352. The fluorinated or chlorinated biphenyl derivatives of Formulae (Ib) or (Id) respectively have a positive dielectric anisotropy if $R_1$ is a cyano group, and have a negative dielectric anisotropy if $R_1$ is alkyl or alkoxy. In these two sub-groups of compounds according to the invention, the halogen substitution also effects a marked widening of the temperature range of the nematic mesophase and a displacement of this range to more favorable temperatures. Depending on the position and the nature of the lateral halogen substituent, the dihalogenocyclohexanes of the partial Formulae (Ie) to (Ih) have a moderate positive dielectric anisotropy (if the lateral substituent is vicinal to the terminal substituent), or the dielectric anisotropy has a value near zero (if the lateral substituent is vicinal to the bond between the two ring systems).

Among the compounds of Formula (I), those of partial Formulae (Ia), (Ib), (Ic), (Id) and (Ig) are preferred, because they can be prepared from more readily accessible starting materials. From among these, the compounds of partial Formula (Ia), if $R_1$ is alkyl having 2–12 C atoms, preferably 3–8 C atoms, and those of partial Formula (Ib) have particularly advantageous properties with a view to their use in liquid crystal display elements.

In the compounds of Formula (I), the alkyl or alkoxy radicals $R_1$ and $R_2$ can be straight-chain or branched. If they are straight-chain, i.e., methyl, ethyl, n-propyl, n-butyl, n-pentyl, n-hexyl, n-heptyl, n-octyl, n-nonyl, n-decyl, n-undecyl or n-dodecyl, or the corresponding alkoxy groups, the corresponding compounds have, as a rule, higher clear points than the compounds with branched wing groups $R_1$ and/or $R_2$. For this reason, usually at most one of the wing groups $R_1$ and $R_2$ contains a branched carbon chain. The compounds of Formula (I) with a branched wing group $R_1$ or $R_2$ are occasionally important due to a higher solubility in the conventional liquid-crystalline base materials, and particularly they are important as chiral doping substances, if they possess optical activity due to the chain branching. Such branched wing groups generally do not contain more than one chain branching. Those branched hydrocarbon radicals R are preferred in which a methyl or ethyl group is present in the 1-position, 2-position or 3-position of a longer carbon chain, for example 2-methylpropyl, 2-methylbutyl, 3-methylbutyl, 2-methylpentyl, 3-methylpentyl, 2-ethylhexyl or 1-methylhexyl.

If $R_1$ and $R_2$ are alkyl or alkoxy, the wing groups $R_1$ and $R_2$ together can contain up to 24 carbon atoms. Within the scope of the present invention, those are preferred among these in which $R_1$ and $R_2$ together contain 3 to 16, in particular 4 to 13, carbon atoms.

The compounds of this invention can be prepared by methods which are fully conventional for substances of this type. Thus, for example, the compounds of Formulae (Ia) or (Ic) can be obtained by diazotizing an aniline derivative of Formula (II)

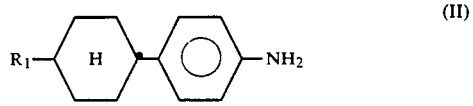
(II)

and reacting the product with copper(I) chloride or copper(I) bromide, respectively, under the conditions of a Sandmeyer reaction. The diazotization and the Sandmeyer reaction are carried out in a manner known per se, as described, for example, in Gattermann-Wieland, Die Praxis des organischen Chemikers [Organic Chemistry in Practice], 40th edition (Walter de Gruyter & Co., Berlin 1961), pages 252–254, which is incorporated by reference herein. The compounds of the Formulae (Ib) and (Id), in which $R_1$ is alkyl or alkoxy, and also the compounds of the Formulae (Ie), (If), (Ig) and (Ih) are obtained by first nitrating a corresponding laterally unsubstituted compound (III)

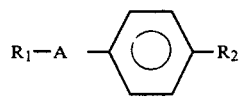
(III)

wherein A and $R_2$ are as defined for Formula (I), to give a compound of Formula (IV)

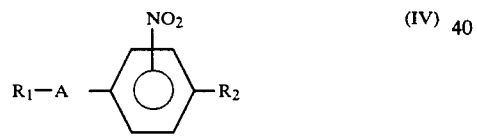
(IV)

reducing the nitro compound (IV) to the amino compound (V)

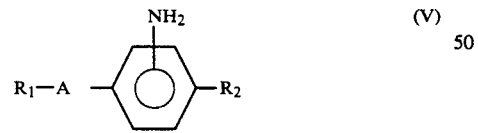
(V)

and reacting the latter, after diazotization, with copper(I) chloride under the conditions of a Sandmeyer reaction, or with a tetrafluoborate under the conditions of a Schiemann-Balz reaction. The nitration of (III) to give (IV) is carried out in the manner conventional for compounds of this type. By suitable selection of the nitrating agent, the temperature, the reaction time and, if appropriate, a solvent or a catalyst, the formation of the possible isomeric nitro compounds—in the ortho-position or meta-position relative to the radical $R_2$, can be directed towards a desired isomer; if appropriate, a resulting mixture of the isomeric nitro compounds is separated to give the individual components in a manner known per se, for example by fractional crystallization or by chromatographic methods. The reduction of (IV) to (V) is likewise carried out in a manner know from the literature, for example by catalytic hydrogenation with tin, zinc or iron and hydrochloric acid, with tin(II) chloride or with dithionite. The diazotization of the amine and the Sandmeyer reaction to give the chloro compounds (Id), (Ig) and (Ih) is carried out in the same way as the above-described synthesis of the comounds (Ia) or (Ic); the Schiemann-Balz synthesis of the compounds (Ib), (Ic) and (If) from the corresponding amine (V) can be carried out according to one of the process variants described in "Organic Reactions", Volume 5 (1949), pages 193–228, which is incorporated by reference herein.

Those compounds of Formula (I), wherein A is 1,4-phenylene, $R_1$ is CN, X is fluoring or chlorine and $R_2$ is alkyl or alkoxy, can be prepared by nitrating the corresponding compound of Formula (VI)

(VI)

to give the nitro compound (VII),

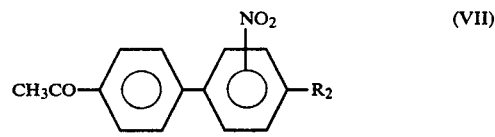
(VII)

reducing the latter to the amino compound (VIII),

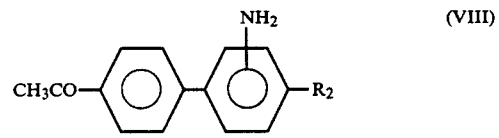
(VIII)

diazotizing (VIII) and then reacting the product with copper(I) chloride under the conditions of a Sandmeyer reaction or with tetrafluoborate under the conditions of a Schiemann-Balz reaction to give the halogen compound (IX),

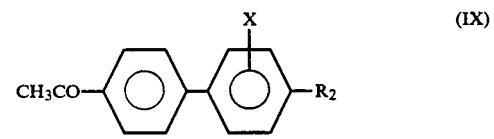
(IX)

which is then reacted with hydroxylamine to give the oxime, from which the amine (X) is prepared by a Beckmann rearrangement known per se:

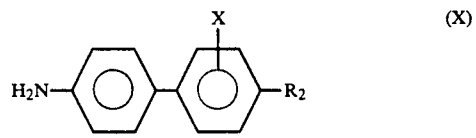
(X)

This amine (X) is then diazotized in a manner conventional per se and the product is reacted with copper(I)

cyanide to give the desired nitrile, under the conditions of a Sandmeyer reaction.

All of the starting materials for this process are either known or readily preparable using fully conventional reactions well-known to those skilled in the art. All of the reactions proceed with retention of trans-configuration of the cyclohexyl rings.

The dielectrics according to this invention comprises 2 to 15, preferably 3 to 12 components, of which at least one is a liquid-crystalline halogen compound of Formula (I). The other constituents are selected from the conventional nematic or nematogenic substances from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4'-bis-cyclohexylbiphenyls, phenyl- or cyclohexyl-pyrimidines, phenyl- or cyclohexyldioxanes, stilbenes which may be halogenated, benzyl phenyl ethers, tolanes and substituted cinnaminc acids. The most important compounds which can be used as constituents of liquid-crystalline dielectrics of this type can be characterized by Formula (XI),

wherein C and D are each a carbocyclic or heterocyclic ring system selected from the group comprising 1,4-disubstituted benzene and cyclohexane rings, 4,4'-disubstituted biphenyl, phenylcyclohexane and cyclohexylcyclohexane systems, 2,5-disubstituted pyrimidine rings and 1,3-dioxane rings, 2,6-disubstituted naphthalene, dihydro- and tetrahydrohaphthalene, quinazoline and tetrahydroquinazoline, B is

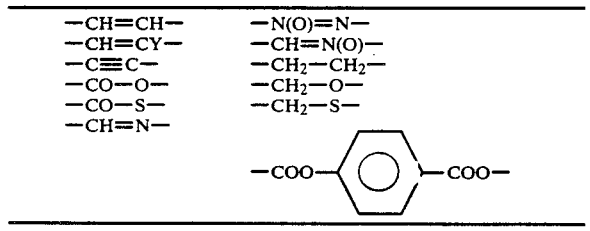

or a C—C single bond, Y is halogen, preferably chlorine, or —CN, and $R_3$ and $R_4$ are alkyl, alkoxy, alkanoyloxy or alkoxycarbonyloxy having up to 18, preferably up to 8, carbon atoms, or one of these radicals can also be —CN, —NC, —NO$_2$, —CH$_3$, F, Cl or Br. In most of these compounds, $R_3$ and $R_4$ are different from one another, one of these radicals being an alkyl group or an alkoxy group in most cases. Other variants of the envisaged substituents, however, are also common. Many such substances, or mixtures thereof, are commercially avaiable.

The dielectrics according to this invention contain, as a rule, at least 30, preferably 50-99, in particular 60-98, percent by weight of the compounds of Formulae (I) and (XI). Of this, preferably at least 5 percent by weight, and in most cases even 10-40 percent by weight, account for one or more compounds of Formula (I). However, the invention also comprises those liquid-crystalline dielectrics to which only less than 5 percent by weight, for example 0.1 to 3 parts by weight, of one or more compounds of Formula (I) have been added, for example for doping purposes. On the other hand, the compounds of Formula (I) can account for up to 60% by weight of the dielectrics according to this invention. Preferably, the liquid-crystalline dielectrics according to this invention contain 10 to 30% by weight of one or more compounds of Formula (I).

The preparation of the dielectrics according to this invention is carried out in a manner conventional per se. As a rule, the desired amount of the components used in a similar quantity is dissolved in the component representing the main constituent, advantageously at an elevated temperature. If a temperature above the clear point of the main constituent is chosen for this, the completeness of the solution process can be observed with particular ease.

The liquid-crystalline dielectrics according to this invention can be modified by suitable additives in such a way that they can be used in all hitherto disclosed types of liquid crystal display elements. Additives of this type are known to those skilled in the art and are extensively described in the relevant literature. For example, it is possible to add dichroic dyes or substances which are intended to modify the dielectric anisotropy, the viscosity, the conductivity and/or the orientation of the nematic phases. Substances of this type are described, for example, in German Offenlegungsschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples, m.p. denotes the melting point, and c.p. denotes the clear point of a liquid-crystalline substance in degrees Centigrade; boiling points are marked b.p.

EXAMPLE 1

189 g of 4-(trans-4-n-propylcyclohexyl)-aniline hydrochloride was suspended in 500 ml of 15% aqueous hydrochloric acid and 300 ml of a 2.5 molar sodium nitrite solution was added thereto at −5° C. in the course of half an hour. This solution was added, at 2° C. in the course of one hour, to a copper(I) salt solution prepared from 250 g of CuSO$_4$ . 5H$_2$O, 88 g of NaCl, 63 g of Na$_2$SO$_3$, 1,000 ml of water and 400 ml of 32% hydrochloric acid. After heating at 40° C. for half an hour, the solution was cooled and extracted 3 times with 300 ml of dichloromethane. The collected organic phases were washed twice with 300 ml of water.

After the solvent had been distilled off, the residue was subjected to a distillation in vacuo, using a spinning band column. The 4-(trans-4-n-propylcyclohexyl)-chlorobenzene distilling over between 105° and 120° C. under 0.01 mm Hg was recrystallized from ethanol; m.p. 36°, c.p. −17°.

The following are prepared analogously:
4-(trans-4-ethylcyclohexyl)-chlorobenzene,
4-(trans-4-n-butylcyclohexyl)-chlorobenzene,
4-(trans-4-n-pentylcyclohexyl)-chlorobenzene,
4-(trans-4-n-hexylcyclohexyl)-chlorobenzene,
4-(trans-4-n-heptylcyclohexyl)-chlorobenzene, 4-(trans-4-n-octylcyclohexyl)-chlorobenzene,
4-(trans-4-n-decylcyclohexyl)-chlorobenzene,
4-(trans-4-n-dodecylcyclohexyl)-chlorobenzene,
4-[trans-4-(2-methylbutyl)-cyclohexyl]-chlorobenzene,
4-[trans-4-(2-ethylhexyl)-cyclohexyl]-chlorobenzene,
4-(trans-4-ethylcyclohexyl)-bromobenzene,
4-(trans-4-n-propylcyclohexyl)-bromobenzene, m.p. 51°, c.p. 0°,
4-(trans-4-n-butylcyclohexyl)-bromobenzene,
4-(trans-4-n-pentylcyclohexyl)-bromobenzene,
4-(trans-4-n-hexylcyclohexyl)-bromobenzene,
4-(trans-4-n-heptylcyclohexyl)-bromobenzene,
4-(trans-4-n-octylcyclohexyl)-bromobenzene,
4-(trans-4-n-decylcyclohexyl)-bromobenzene,
4-(trans-4-n-dodecylcyclohexyl)-bromobenzene,
4-[trans-4-(2-methylbutyl)-cyclohexyl]-bromobenzene and
4-[trans-4-(2-ethylhexyl)-cyclohexyl]-bromobenzene.

EXAMPLE 2

(a) 37 g of 4-n-hexyloxy-4'-n-pentyl-biphenyl was dissolved in 100 ml of dichloromethane, and 14 ml of 65% nitric acid was added to this solution at 5° C. with intensive stirring. After stirring for 1.5 hours, the mixture was poured into 500 ml of water, and the organic phase was separated off. After washing several times with water, the dichloromethane was distilled off. The oily residue was dissolved in 300 ml of methanol and, after the addition of 10 g of Raney nickel, hydrogenated at room temperature under normal pressure; the absorption of hydrogen ceased after 1 hour. After the catalyst had been filtered off, the methanol was distilled off, the residue was dissolved in 25 ml of toluene and the solution was passed over a chromatography column (silica gel, toluene as solvent). The main fraction was concentrated and freed from the solvent by distillation. This gave 20 g of 3-amino-4-n-hexyloxy-4'-n-pentyl-biphenyl, c.p. (smectic-isotropic) 70°.

(b) 16.5 g of 3-amino-4-n-hexyloxy-4'-n-pentyl-biphenyl was stirred into 15 ml of 36% aqueous hydrochloric acid. After 10 ml of dioxane had been added, the solution of 3.0 g of sodium nitrite in 12 ml of water was added dropwise at 0° to the above solution. Immediately after this, and likewise at 0°, a solution of 15 g of sodium tetrafluoborate in 25 ml of water was added dropwise. The precipitate which formed was filtered off after 2 hours, washed with ice water and dried under reduced pressure at room temperature. The dry powder of diazonium tetrafluoborate was heated to 120°, until the evolution of gas ceased, and the remaining 3-fluoro-4-n-hexyloxy-4'-n-pentyl-biphenyl was subjected to distillation in a bulb tube under the vacuum of a mercury diffusion pump; c.p. (smectic-isotropic) 84°.

The following are prepared analogously:
3-fluoro-4-methoxy-4'-n-propylbiphenyl,
3-fluoro-4-methoxy-4'-n-butylbiphenyl,
3-fluoro-4-methoxy-4'-n-pentylbiphenyl,
3-fluoro-4-methoxy-4'-n-hexylbiphenyl,
3-fluoro-4-methoxy-4'-n-heptylbiphenyl,
3-fluoro-4-methoxy-4'-n-octylbiphenyl,
3-fluoro-4-methoxy-4'-n-nonylbiphenyl,
3-fluoro-4-methoxy-4'-n-decylbiphenyl,
3-fluoro-4-methoxy-4'-n-undecylbiphenyl,
3-fluoro-4-methoxy-4'-n-dodecylbiphenyl,
3-fluoro-4-methoxy-4'-n-(2-methylbutyl)-biphenyl,
3-fluoro-4-ethoxy-4'-ethylbiphenyl,
3-fluoro-4-ethoxy-4'-n-propylbiphenyl,
3-fluoro-4-ethoxy-4'-n-butylbiphenyl,
3-fluoro-4-ethoxy-4'-n-pentylbiphenyl,
3-fluoro-4-ethoxy-4'-n-hexylbiphenyl,
3-fluoro-4-ethoxy-4'-n-heptylbiphenyl,
3-fluoro-4-ethoxy-4'-n-octylbiphenyl,
3-fluoro-4-ethoxy-4'-n-nonylbiphenyl,
3-fluoro-4-ethoxy-4'-n-decylbiphenyl,
3-fluoro-4-ethoxy-4'-n-undecylbiphenyl,
3-fluoro-4-ethoxy-4'-n-dodecylbiphenyl,
3-fluoro-4-ethoxy-4'-(2-methylbutyl)-biphenyl,
3-fluoro-4-n-propoxy-4'-methylbiphenyl,
3-fluoro-4-n-propoxy-4'-ethylbiphenyl,
3-fluoro-4-n-propoxy-4'-n-propylbiphenyl,
3-fluoro-4-n-propoxy-4'-n-butylbiphenyl,
3-fluoro-4-n-propoxy-4'-n-pentylbiphenyl,
3-fluoro-4-n-propoxy-4'-n-hexylbiphenyl,
3-fluoro-4-n-propoxy-4'-n-heptylbiphenyl,
3-fluoro-4-n-propoxy-4'-n-octylbiphenyl,
3-fluoro-4-n-propoxy-4'-n-nonylbiphenyl,
3-fluoro-4-n-propoxy-4'-n-decylbiphenyl,
3-fluoro-4-n-propoxy-4'-n-undecylbiphenyl,
3-fluoro-4-n-propoxy-4'-n-dodecylbiphenyl,
3-fluoro-4-n-propoxy-4'-(2-methylbutyl)-biphenyl,
3-fluoro-4-n-butoxy-4'-methylbiphenyl,
3-fluoro-4-n-butoxy-4'-ethylbiphenyl,
3-fluoro-4-n-butoxy-4'-n-propylbiphenyl,
3-fluoro-4-n-butoxy-4'-n-butylbiphenyl,
3-fluoro-4-n-butoxy-4'-n-pentylbiphenyl,
3-fluoro-4-n-butoxy-4'-n-hexylbiphenyl,
3-fluoro-4-n-butoxy-4'-n-heptylbiphenyl,
3-fluoro-4-n-butoxy-4'-n-octylbiphenyl,
3-fluoro-4-n-butoxy-4'-n-nonylbiphenyl,
3-fluoro-4-n-butoxy-4'-n-decylbiphenyl,
3-fluoro-4-n-butoxy-4'-n-undecylbiphenyl,
3-fluoro-4-n-butoxy-4'-n-dodecylbiphenyl,
3-fluoro-4-n-butoxy-4'-(2-methylbutyl)-biphenyl,
3-fluoro-4-n-pentyloxy-4'-methylbiphenyl,
3-fluoro-4-n-pentyloxy-4'-ethylbiphenyl,
3-fluoro-4-n-pentyloxy-4'-n-propylbiphenyl,
3-fluoro-4-n-pentyloxy-4'-n-butylbiphenyl,
3-fluoro-4-n-pentyloxy-4'-n-pentylbiphenyl,
3-fluoro-4-n-pentyloxy-4'-n-hexylbiphenyl,
3-fluoro-4-n-pentyloxy-4'-n-heptylbiphenyl,
3-fluoro-4-n-pentyloxy-4'-n-octylbiphenyl,
3-fluoro-4-n-pentyloxy-4'-n-nonylbiphenyl,
3-fluoro-4-n-pentyloxy-4'-n-decylbiphenyl,
3-fluoro-4-n-pentyloxy-4'-n-undecylbiphenyl,
3-fluoro-4-n-pentyloxy-4'-(2-methylbutyl)-biphenyl,
3-fluoro-4-n-hexyloxy-4'-methylbiphenyl,
3-fluoro-4-n-hexyloxy-4'-ethylbiphenyl,
3-fluoro-4-n-hexyloxy-4'-n-propylbiphenyl,
3-fluoro-4-n-hexyloxy-4'-n-butylbiphenyl,
3-fluoro-4-n-hexyloxy-4'-n-hexylbiphenyl,
3-fluoro-4-hexyloxy-4'-n-heptylbiphenyl,
3-fluoro-4-n-hexyloxy-4'-n-octylbiphenyl,
3-fluoro-4-n-hexyloxy-4'-n-nonylbiphenyl,
3-fluoro-4-n-hexyloxy-4'-n-decylbiphenyl,
3-fluoro-4-n-hexyloxy-4'-(2-methylbutyl)-biphenyl,
3-fluoro-4-n-heptyloxy-4'-methylbiphenyl,
3-fluoro-4-n-heptyloxy-4'-ethylbiphenyl,
3-fluoro-4-n-heptyloxy-4'-n-propylbiphenyl,
3-fluoro-4-n-heptyloxy-4'-n-butylbiphenyl,
3-fluoro-4-n-heptyloxy-4'-n-pentylbiphenyl,
3-fluoro-4-n-heptyloxy-4'-n-hexylbiphenyl,
3-fluoro-4-n-heptyloxy-4'-n-heptylbiphenyl,
3-fluoro-4-n-heptyloxy-4'-n-octylbiphenyl,
3-fluoro-4-n-heptyloxy-4'-(2-methylbutyl)-biphenyl,
3-fluoro-4-n-octyloxy-4'-methylbiphenyl,
3-fluoro-4-n-octyloxy-4'-ethylbiphenyl, 3-fluoro-4-n-octyloxy-4'-n-propylbiphenyl,
3-fluoro-4-n-octyloxy-4'-n-butylbiphenyl,
3-fluoro-4-n-octyloxy-4'-n-pentylbiphenyl,
3-fluoro-4-n-octyloxy-4'-n-hexylbiphenyl,
3-fluoro-4-n-octyloxy-4'-n-heptylbiphenyl,
3-fluoro-4-n-octyloxy-4'-(2-methylbutyl)-biphenyl,
3-fluoro-4-(2-ethylhexyloxy)-4'-methylbiphenyl,
3-fluoro-4-(2-ethylhexyloxy)-4'-ethylbiphenyl,
3-fluoro-4-(2-ethylhexyloxy)-4'-n-propylbiphenyl,
3-fluoro-4-(2-ethylhexyloxy)-4'-n-butylbiphenyl,
3-fluoro-4-(2-ethylhexyloxy)-4'-n-pentylbiphenyl,
3-fluoro-4-(2-ethylhexyloxy)-4'-n-hexylbiphenyl,
3-fluoro-4-(2-ethylhexyloxy)-4'-n-heptylbiphenyl and
3-fluoro-4-(2-ethylhexyloxy)-4'-n-octylbiphenyl.

EXAMPLE 3

(a) 59 g of 4,4'-di-n-pentyl-biphenyl in the solid form was introduced into a warm mixture, at 40°, of 40 ml of 65% nitric acid and 48 ml of 96% sulphuric acid. After the end of the addition, the mixture was stirred for 1 further hour at 60° and poured onto 600 g of ice. The 4,4'-di-n-pentyl-2-nitro-biphenyl which had crystallized out was filtered off and recrystallized from ethanol. (b) 34 g of 4,4'-di-n-pentyl-2-nitro-biphenyl was dissolved in 200 ml of tetrahydrofuran. After the addition of 3 g of palladium-on-carbon (10% of Pd), hydrogen was passed into the mixture for 1 hour under normal pressure and at room temperature. The catalyst was then filtered off and the filtrate was evaporated. The remaining 2-amino-4,4'-di-n-pentyl-biphenyl was recrystallized from petroleum ether (boiling range 40°–60°). (c) 15.5 g of 2-amino-4,4'-di-n-pentyl-biphenyl was converted, analogously to Example 2, by reaction with nitrous acid, sodium tetrafluoborate, heating and by high-vacuum distillation and recrystallization from ethanol into 2-fluoro-4,4'-di-n-pentyl-biphenyl; m.p. −3°, c.p. −35°.

The following are prepared analogously:
2-fluoro-4-methyl-4'-n-propylbiphenyl,
2-fluoro-4-methyl-4'-n-butylbiphenyl,
2-fluoro-4-methyl-4'-n-pentylbiphenyl,
2-fluoro-4-methyl-4'-n-hexylbiphenyl,
2-fluoro-4-methyl-4'-n-heptylbiphenyl,
2-fluoro-4-methyl-4'-n-octylbiphenyl,
2-fluoro-4-methyl-4'-n-nonylbiphenyl,
2-fluoro-4-methyl-4'-n-decylbiphenyl,
2-fluoro-4-methyl-4'-n-undecylbiphenyl,
2-fluoro-4-methyl-4'-n-dodecylbiphenyl,
2-fluoro-4-methyl-4'-(2-methylbutyl)-biphenyl,
2-fluoro-4-ethyl-4'-methylbiphenyl,
2-fluoro-4-ethyl-4'-ethylbiphenyl,
2-fluoro-4-ethyl-4'-n-propylbiphenyl,
2-fluoro-4-ethyl-4'-n-butylbiphenyl,
2-fluoro-4-ethyl-4'-n-pentylbiphenyl,
2-fluoro-4-ethyl-4'-n-hexylbiphenyl,
2-fluoro-4-ethyl-4'-n-heptylbiphenyl,
2-fluoro-4-ethyl-4'-n-octylbiphenyl,
2-fluoro-4-ethyl-4'-n-nonylbiphenyl,
2-fluoro-4-ethyl-4'-n-decylbiphenyl,
2-fluoro-4-ethyl-4'-n-undecylbiphenyl,
2-fluoro-4-ethyl-4'-n-dodecylbiphenyl,
2-fluoro-4-ethyl-4'-(2-methylbutyl)-biphenyl,
2-fluoro-4-n-propyl-4'-methylbiphenyl,
2-fluoro-4-n-propyl-4'-ethylbiphenyl,
2-fluoro-4-n-propyl-4'-n-propylbiphenyl,
2-fluoro-4-n-propyl-4'-n-butylbiphenyl,
2-fluoro-4-n-propyl-4'-n-pentylbiphenyl,
2-fluoro-4-n-propyl-4'-n-hexylbiphenyl,
2-fluoro-4-n-propyl-4'-n-heptylbiphenyl,
2-fluoro-4-n-propyl-4'-n-octylbiphenyl,
2-fluoro-4-n-propyl-4'-n-nonylbiphenyl,
2-fluoro-4-n-propyl-4'-n-decylbiphenyl,
2-fluoro-4-n-propyl-4'-n-undecylbiphenyl,
2-fluoro-4-n-propyl-4'-n-dodecylbiphenyl,
2-fluoro-4-n-propyl-4'-(2-methylbutyl)-biphenyl,
2-fluoro-4-n-butyl-4'-methylbiphenyl,
2-fluoro-4-n-butyl-4'-ethylbiphenyl,
2-fluoro-4-n-butyl-4'-n-propylbiphenyl,
2-fluoro-4-n-butyl-4'-n-butylbiphenyl,
2-fluoro-4-n-butyl-4'-n-pentylbiphenyl,
2-fluoro-4-n-butyl-4'-n-hexylbiphenyl,
2-fluoro-4-n-butyl-4'-n-heptylbiphenyl,
2-fluoro-4-n-butyl-4'-n-octylbiphenyl,
2-fluoro-4-n-butyl-4'-n-nonylbiphenyl,
2-fluoro-4-n-butyl-4'-n-decylbiphenyl,
2-fluoro-4-n-butyl-4'-n-undecylbiphenyl,
2-fluoro-4-n-butyl-4'-n-dodecylbiphenyl,
2-fluoro-4-n-butyl-4'-(2-methylbutyl)-biphenyl,
2-fluoro-4-n-pentyl-4'-methylbiphenyl,
2-fluoro-4-n-pentyl-4'-ethylbiphenyl,
2-fluoro-4-n-pentyl-4'-n-propylbiphenyl,
2-fluoro-4-n-pentyl-4'-n-butylbiphenyl,
2-fluoro-4-n-pentyl-4'-n-hexylbiphenyl,
2-fluoro-4-n-pentyl-4'-n-heptylbiphenyl,
2-fluoro-4-n-pentyl-4'-n-octylbiphenyl,
2-fluoro-4-n-pentyl-4'-n-nonylbiphenyl,
2-fluoro-4-n-pentyl-4'-n-decylbiphenyl,
2-fluoro-4-n-pentyl-4'-n-undecylbiphenyl,
2-fluoro-4-n-pentyl-4'-(2-methylbutyl)-biphenyl,
2-fluoro-4-n-hexyl-4'-methylbiphenyl,
2-fluoro-4-n-hexyl-4'-ethylbiphenyl,
2-fluoro-4-n-hexyl-4'-n-propylbiphenyl,
2-fluoro-4-n-hexyl-4'-n-butylbiphenyl,
2-fluoro-4-n-hexyl-4'-n-pentylbiphenyl,
2-fluoro-4-n-hexyl-4'-n-hexylbiphenyl,
2-fluoro-4-n-hexyl-4'-n-heptylbiphenyl,
2-fluoro-4-n-hexyl-4'-n-octylbiphenyl,
2-fluoro-4-n-hexyl-4'-n-nonylbiphenyl,
2-fluoro-4-n-hexyl-4'-n-decylbiphenyl,
2-fluoro-4-n-hexyl-4'-(2-methylbutyl)-biphenyl,
2-fluoro-4-n-heptyl-4'-methylbiphenyl,
2-fluoro-4-n-heptyl-4'-ethylbiphenyl,
2-fluoro-4-n-heptyl-4'-n-propylbiphenyl,
2-fluoro-4-n-heptyl-4'-n-butylbiphenyl,
2-fluoro-4-n-heptyl-4'-n-pentylbiphenyl,
2-fluoro-4-n-heptyl-4'-n-hexylbiphenyl,
2-fluoro-4-n-heptyl-4'-n-heptylbiphenyl,
2-fluoro-4-n-heptyl-4'-n-octylbiphenyl,
2-fluoro-4-n-heptyl-4'-(2-methylbutyl)-biphenyl,
2-fluoro-4-n-octyl-4'-methylbiphenyl,
2-fluoro-4-n-octyl-4'-ethylbiphenyl,
2-fluoro-4-n-octyl-4'-n-propylbiphenyl,
2-fluoro-4-n-octyl-4'-n-butylbiphenyl,
2-fluoro-4-n-octyl-4'-n-pentylbiphenyl,
2-fluoro-4-n-octyl-4'-n-hexylbiphenyl,
2-fluoro-4-n-octyl-4'-n-heptylbiphenyl and
2-fluoro-4-n-octyl-4'-(2-methylbutyl)-biphenyl.

EXAMPLE 4

(a) 15 g of 4-n-butoxy-4'-n-pentylbiphenyl was nitrated and then reduced analogously to Example (2a). This gave 10 g of 3-amino-4-n-butoxy-4'-n-pentylbiphenyl. (b) 10 g of 3-amino-4-n-butoxy-4'-n-pentylbiphenyl was, analogously to Example 1, converted into 3-chloro-4-n-butoxy-4'-n-pentylbiphenyl; m.p. 38°, c.p. −40°.

The following are prepared analogously:

3-chloro-4-methoxy-4'-n-propylbiphenyl,
3-chloro-4-ethoxy-4'-n-propylbiphenyl,
3-chloro-4-n-propoxy-4'-n-propylbiphenyl,
3-chloro-4-n-butoxy-4'-n-propylbiphenyl,
3-chloro-4-n-pentyloxy-4'-n-propylbiphenyl,
3-chloro-4-n-hexyloxy-4'-n-propylbiphenyl,
3-chloro-4-n-heptyloxy-4'-n-propylbiphenyl,
3-chloro-4-n-octyloxy-4'-n-propylbiphenyl,
3-chloro-4-n-nonyloxy-4'-n-propylbiphenyl,
3-chloro-4-n-decyloxy-4'-n-propylbiphenyl,
3-chloro-4-n-propoxy-4'-methylbiphenyl,
3-chloro-4-n-butoxy-4'-methylbiphenyl,
3-chloro-4-n-pentyloxy-4'-methylbiphenyl,
3-chloro-4-n-hexyloxy-4'-methylbiphenyl,
3-chloro-4-n-heptyloxy-4'-methylbiphenyl,
3-chloro-4-n-octyloxy-4'-methylbiphenyl,
3-chloro-4-n-nonyloxy-4'-methylbiphenyl,
3-chloro-4-n-decyloxy-4'-methylbiphenyl,
3-chloro-4-n-ethoxy-4'-ethylbiphenyl,
3-chloro-4-n-propoxy-4'-ethylbiphenyl,
3-chloro-4-n-butoxy-4'-ethylbiphenyl,
3-chloro-4-n-pentyloxy-4'-ethylbiphenyl,
3-chloro-4-n-hexyloxy-4'-ethylbiphenyl,
3-chloro-4-n-heptyloxy-4'-ethylbiphenyl,
3-chloro-4-n-octyloxy-4'-ethylbiphenyl,
3-chloro-4-n-nonyloxy-4'-ethylbiphenyl,
3-chloro-4-n-decyloxy-4'-ethylbiphenyl,
3-chloro-4-methoxy-4'-n-butylbiphenyl,
3-chloro-4-ethoxy-4'-n-butylbiphenyl,
3-chloro-4-n-propoxy-4'-n-butylbiphenyl,
3-chloro-4-n-butoxy-4'-n-butylbiphenyl,
3-chloro-4-n-pentyloxy-4'-n-butylbiphenyl,
3-chloro-4-n-hexyloxy-4'-n-butylbiphenyl,
3-chloro-4-n-heptyloxy-4'-n-butylbiphenyl,
3-chloro-4-n-octyloxy-4'-n-butylbiphenyl,
3-chloro-4-n-nonyloxy-4'-n-butylbiphenyl,
3-chloro-4-n-decyloxy-4'-n-butylbiphenyl,
3-chloro-4-methoxy-4'-n-pentylbiphenyl,
3-chloro-4-ethoxy-4'-n-pentylbiphenyl,
3-chloro-4-n-propoxy-4'-n-pentylbiphenyl,
3-chloro-4-n-butoxy-4'-n-pentylbiphenyl,
3-chloro-4-n-pentyloxy-4'-n-pentylbiphenyl,
3-chloro-4-n-hexyloxy-4'-n-pentylbiphenyl,
3-chloro-4-n-heptyloxy-4'-n-pentylbiphenyl,
3-chloro-4-n-octyloxy-4'-n-pentylbiphenyl,
3-chloro-4-methoxy-4'-n-hexylbiphenyl,
3-chloro-4-ethoxy-4'-n-hexylbiphenyl,
3-chloro-4-n-propoxy-4'-n-hexylbiphenyl,
3-chloro-4-n-butoxy-4'-n-hexylbiphenyl,
3-chloro-4-n-pentyloxy-4'-n-hexylbiphenyl,
3-chloro-4-n-hexyloxy-4'-n-hexylbiphenyl,
3-chloro-4-n-heptyloxy-4'-n-hexylbiphenyl,
3-chloro-4-n-octyloxy-4'-n-hexylbiphenyl,
3-chloro-4-methoxy-4'-n-heptylbiphenyl,
3-chloro-4-ethoxy-4'-n-heptylbiphenyl,
3-chloro-4-n-propoxy-4'-n-heptylbiphenyl,
3-chloro-4-n-butoxy-4'-n-heptylbiphenyl,
3-chloro-4-n-pentyloxy-4'-n-heptylbiphenyl,
3-chloro-4-n-hexyloxy-4'-n-heptylbiphenyl,
3-chloro-4-methoxy-4'-n-octylbiphenyl,
3-chloro-4-ethoxy-4'-n-octylbiphenyl,
3-chloro-4-n-propoxy-4'-n-octylbiphenyl,
3-chloro-4-n-butoxy-4'-n-octylbiphenyl,
3-chloro-4-n-pentyloxy-4'-n-octylbiphenyl and
3-chloro-4-n-hexyloxy-4'-n-octylbiphenyl.

EXAMPLE 5

(a) 26 g of 4-(trans-4-n-pentylcyclohexyl)-phenetole was nitrated and then reduced analogously to Example (2a). This gave 16 g of 2-amino-4-(trans-4-n-pentylcyclohexyl)-phenetole. (b) Analogously to Example (2b), 14 g of 2-amino-4-(trans-4-n-pentylcyclohexyl)-phenetole was diazotized, the product was reacted with sodium tetrafluoborate and the diazonium tetrafluoborate was thermally decomposed. The remaining 2-fluoro-4-(trans-4-n-pentylcyclohexyl)-phenetole was recrystallized from ethanol.

The following are prepared analogously:
2-fluoro-4-(trans-4-methylcyclohexyl)-n-propoxybenzene,
2-fluoro-4-(trans-4-methylcyclohexyl)-n-butoxybenzene,
2-fluoro-4-(trans-4-methylcyclohexyl)-n-pentyloxybenzene,
2-fluoro-4-(trans-4-methylcyclohexyl)-n-hexyloxybenzene,
2-fluoro-4-(trans-4-methylcyclohexyl)-n-heptyloxybenzene,
2-fluoro-4-(trans-4-methylcyclohexyl)-n-octyloxybenzene,
2-fluoro-4-(trans-4-methylcyclohexyl)-n-decyloxybenzene,
2-fluoro-4-(trans-4-methylcyclohexyl)-n-dodecyloxybenzene,
2-fluoro-4-(trans-4-ethylcyclohexyl)-phenetole,
2-fluoro-4-(trans-4-ethylcyclohexyl)-n-propoxybenzene,
2-fluoro-4-(trans-4-ethylcyclohexyl)-n-butoxybenzene,
2-fluoro-4-(trans-4-ethylcyclohexyl)-n-pentyloxybenzene,
2-fluoro-4-(trans-4-ethylcyclohexyl)-n-hexyloxybenzene,
2-fluoro-4-(trans-4-ethylcyclohexyl)-n-heptyloxybenzene,
2-fluoro-4-(trans-4-ethylcyclohexyl)-n-octyloxybenzene,
2-fluoro-4-(trans-4-ethylcyclohexyl)-n-decyloxybenzene,
2-fluoro-4-(trans-4-ethylcyclohexyl)-n-dodecyloxybenzene,
2-fluoro-4-(trans-4-ethylcyclohexyl)-(1-methylbutoxy)-benzene,
2-fluoro-4-(trans-4-n-propylcyclohexyl)-phenetole,
2-fluoro-4-(trans-4-n-propylcyclohexyl)-n-propoxybenzene,
2-fluoro-4-(trans-4-n-propylcyclohexyl)-n-butoxybenzene,
2-fluoro-4-(trans-4-n-propylcyclohexyl)-n-pentyloxybenzene,
2-fluoro-4-(trans-4-n-propylcyclohexyl)-n-hexyloxybenzene,
2-fluoro-4-(trans-4-n-propylcyclohexyl)-n-heptyloxybenzene,
2-fluoro-4-(trans-4-n-propylcyclohexyl)-n-octyloxybenzene,
2-fluoro-4-(trans-4-n-propylcyclohexyl)-n-decyloxybenzene,
2-fluoro-4-(trans-4-n-propylcyclohexyl)-n-dodecyloxybenzene,
2-fluoro-4-(trans-4-n-butylcyclohexyl)-anisole,
2-fluoro-4-(trans-4-n-butylcyclohexyl)-phenetole,
2-fluoro-4-(trans-4-n-butylcyclohexyl)-n-propoxybenzene, 2-fluoro-4-(trans-4-n-butylcyclohexyl)-n-butoxybenzene,
2-fluoro-4-(trans-4-n-butylcyclohexyl)-n-pentyloxybenzene,
2-fluoro-4-(trans-4-n-butylcyclohexyl)-n-hexyloxybenzene,
2-fluoro-4-(trans-4-n-butylcyclohexyl)-n-heptyloxybenzene,
2-fluoro-4-(trans-4-n-butylcyclohexyl)-n-octyloxybenzene,
2-fluoro-4-(trans-4-n-butylcyclohexyl)-n-decyloxybenzene,
2-fluoro-4-(trans-4-n-butylcyclohexyl)-n-dodecyloxybenzene,
2-fluoro-4-(trans-4-n-butylcyclohexyl)-(1-methylbutoxy)-benzene,
2-fluoro-4-(trans-4-n-pentylcyclohexyl)-anisole,
2-fluoro-4-(trans-4-n-pentylcyclohexyl)-n-propoxybenzene,
2-fluoro-4-(trans-4-n-pentylcyclohexyl)-n-butoxybenzene,
2-fluoro-4-(trans-4-n-pentylcyclohexyl)-n-pentyloxybenzene,
2-fluoro-4-(trans-4-n-pentylcyclohexyl)-n-hexyloxybenzene,
2-fluoro-4-(trans-4-n-pentylcyclohexyl)-n-heptyloxybenzene,
2-fluoro-4-(trans-4-n-pentylcyclohexyl)-n-octyloxybenzene,
2-fluoro-4-(trans-4-n-heptylcyclohexyl)-anisole,
2-fluoro-4-(trans-4-n-heptylcyclohexyl)-phenetole,
2-fluoro-4-(trans-4-n-heptylcyclohexyl)-n-propoxybenzene,
2-fluoro-4-(trans-4-n-heptylcyclohexyl)-n-butoxybenzene,
2-fluoro-4-(trans-4-n-heptylcyclohexyl)-n-pentyloxybenzene,
2-fluoro-4-(trans-4-n-heptylcyclohexyl)-n-hexyloxybenzene,
2-fluoro-4-(trans-4-n-heptylcyclohexyl)-n-heptyloxybenzene and
2-fluoro-4-(trans-4-n-heptylcyclohexyl)-(1-methylbutoxy)-benzene.

The examples which follow relate to dielectrics of this invention, containing at least one compound of Formula (I).

EXAMPLE 6

A liquid-crystalline dielectric composed of
20% of 4-ethoxyphenyl trans-4-propylcyclohexanecarboxylate,
20% of 4-ethoxyphenyl trans-4-n-butylcyclohexanecarboxylate,
20% of 4-methoxyphenyl trans-4-n-pentylcyclohexanecarboxylate,
30% of 4-(trans-4-n-propylcyclohexyl)-chlorobenzene and
10% of 4-(trans-4-n-propylcyclohexyl)-phenyl trans-4-n-butylcyclohexanecarboxylate
has a nematic phase in the temperature range from $-3°$ to $+55°$, a dielectric anisotropy of $\Delta\epsilon = +0.9$ and an astonishingly low viscosity of only $12 \times 10^{-3}$ Pa.s at 20°.

EXAMPLE 7

A liquid-crystalline dielectric composed of
40% of 4-n-pentyl-4'-cyanobiphenyl,
30% of 4-(trans-4-n-pentylcyclohexyl)-chlorobenzene,
15% of 4-(trans-4-n-pentylcyclohexyl)-4'-ethylbiphenyl and
15% of 4-(trans-4-n-propylcyclohexyl)-4'-ethylbiphenyl
has a nematic phase in the temperature range from $-7°$ to $+54°$, a dielectric anisotropy of $\Delta\epsilon = +6.7$, an optical anisotropy of $\Delta n = 0.18$ and a viscosity of only $14 \times 10^{-3}$ Pa.s at 20°. By virtue of this low viscosity and the comparatively high optical and dielectric anisotropies, this dielectric is very suitable for liquid crystal display elements based on the twisted nematic cell.

EXAMPLE 8

A liquid-crystalline dielectric composed of 27% of 4-(trans-4-n-propylcyclohexyl)-chlorobenzene,
18% of 4-ethoxyphenyl trans-4-n-propylcyclohexanecarboxylate,
18% of 4-ethoxyphenyl trans-4-n-butylcyclohexanecarboxylate,
17% of 4-(trans-4-n-propylcyclohexyl)-phenyl trans-4-n-butylcyclohexanecarboxylate,
10% of 2-(4-cyanophenyl)-5-n-propyl-1,3-dioxane and
10% of 2-(4-cyanophenyl)-5-n-butyl-1,3-dioxane
has a nematic phase in the temperature range from $-6°$ to $+57°$, a dielectric anisotropy of $\Delta\epsilon = +7$ and a viscosity of only $16 \times 10^{-3}$ Pa.s. In liquid crystal display elements based on the twisted nematic cell, this dielectric has a steep characteristic and is therefore very suitable for displays driven in multiplex operation.

EXAMPLE 9

A liquid-crystalline dielectric composed of
30% of 4-n-pentyl-4'-cyanobiphenyl,
25% of 4-(trans-4-n-butylcyclohexyl)-chlorobenzene,
18% of 4-(trans-4-n-propylcyclohexyl)-benzonitrile,
10% of 4-(trans-4-n-pentylcyclohexyl)-4'-(trans-4-n-propylcyclohexyl)-biphenyl,
9% of 4-(trans-4-n-pentylcyclohexyl)-4'-cyanobiphenyl and
8% of 4-n-pentyl-4''-cyanoterphenyl
has a nematic phase in the temperature range from $-9°$ to $+75°$, a dielectric anisotrophy of $\Delta\epsilon = +9.4$, an optical anisotropy of $\Delta n = +0.18$ and a viscosity of only $21 \times 10^{-3}$ Pa.s. at 20°. It is very suitable for large-area, fast-switching display elements based on the twisted nematic cell.

EXAMPLE 10

A liquid-crystalline dielectric composed of
27% of 4-(trans-4-n-heptylcyclohexyl)-chlorobenzene,
23% of 4-(trans-4-n-pentylcyclohexyl)-2'-fluoro-4'-ethylbiphenyl,
22% of 4-(trans-4-n-pentylcyclohexyl)-4'-ethylbiphenyl,
18% of 4-(trans-4-n-propylcyclohexyl)-benzonitrile and
10% of 4-(trans-4-n-pentylcyclohexyl)-4'-(trans-4-n-propylcyclohexyl)-biphenyl
has a nematic phase in the temperature range from $-9°$ to $+95°$, a dielectric anisotropy of $\Delta\epsilon = +3.8$ and a viscosity of $19 \times 10^{-3}$ Pa.s at 20°, which even at 0° does not rise to more than $55 \times 10^{-3}$. This dielectric is very suitable for liquid crystal display elements which are operated under extreme temperature conditions.

EXAMPLE 11

A liquid-crystalline dielectric composed of
15% of 4-(trans-4-n-propylcyclohexyl)-benzonitrile,
11% of 4-(trans-4-n-butylcyclohexyl)-benzonitrile,
21% of 4-(trans-4-n-pentylcyclohexyl)-benzonitrile, 21% of 4-(trans-4-n-pentylcyclohexyl)-4'-ethylbiphenyl,
4% of 4-(trans-4-n-pentylcyclohexyl)-4'-cyanobiphenyl,
12% of 4-(trans-4-n-pentylcyclohexyl)-4'-(trans-4-n-propylcyclohexyl)-biphenyl and
16% of 4,4'-bis-n-pentyl-2-fluorobiphenyl
has a nematic phase in the temperature range from −20° to +90°, a dielectric anisotropy of $\Delta\epsilon = 10.5$ and a viscosity of only $20 \times 10^{-3}$ Pa.s. It is especially suitable for use in display elements based on the twisted nematic cell under extreme temperature conditions.

EXAMPLE 12

A liquid-crystalline dielectric composed of
25% of 4-(trans-4-ethylcyclohexyl)-chlorobenzene,
20% of 4-(trans-4-n-propylcyclohexyl)-phenetole,
15% of 4-(trans-4-n-propylcyclohexyl)-ethylbenzene,
15% of 4-(trans-4-n-propylcyclohexyl)-4'-ethylbiphenyl,
15% of 4-(trans-4-n-pentylcyclohexyl)-4'-ethylbiphenyl and
10% of 4-(trans-4-n-pentylcyclohexyl)-4'-(trans-4-n-propylcyclohexyl)-biphenyl
has a nematic phase in the temperature range from −13 to +62° and a viscosity of only $9 \times 10^{-3}$ Pa.s at 20°.

EXAMPLE 13

A liquid-crystalline dielectric composed of
27% of 4-(trans-4-n-propylcyclohexyl)-chlorobenzene,
18% of 4-(trans-4-n-propylcyclohexyl)-benzonitrile,
16% of 4-(trans-4-n-propylcyclohexyl)-phenetole,
22% of 4-(trans-4-n-pentylcyclohexyl)-4'-ethylbiphenyl,
7% of 4-(trans-4-n-pentylcyclohexyl)-4'-cyanobiphenyl and
10% of 4-(trans-4-n-pentylcyclohexyl)-biphenyl
has a nematic phase in the temperature range from −15° to +86° and a viscosity of only $15 \times 10^{-3}$ Pa.s at 20°; even at 0°, the viscosity rises only to $48 \times 10^{-3}$.

The preceding examples can be repeated with similar success by substituting the generically or specifically described reactants and/or operatingconditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A liquid-crystalline halogen compound of the formula

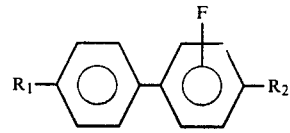

wherein $R_1$ is alkyl or alkoxy each of 1 to 12 carbon atoms or cyano; and $R_2$ is alkyl or alkoxy each of 1 to 12 carbon atoms; with the proviso that $R_1$ and $R_2$ are not simultaneously methyl.

2. A liquid-crystalline halogen compound of claim 1 wherein $R_1$ is alkyl of 3–8 carbon atoms.

3. A compound of claim 1, wherein $R_1$ is alkyl or alkoxy.

* * * * *